US00PP34183P2

(12) United States Plant Patent
Bradford et al.

(10) Patent No.: US PP34,183 P2
(45) Date of Patent: May 3, 2022

(54) PLUM TREE NAMED 'BLACKRED XVI'

(50) Latin Name: *Prunus salicina*
Varietal Denomination: BLACKRED XVI

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,906

(22) Filed: Dec. 17, 2021

(51) Int. Cl.
*A01H 6/74* (2018.01)
*A01H 5/08* (2018.01)

(52) U.S. Cl.
USPC ..... Plt./184

(58) Field of Classification Search
USPC ..... Plt./184
See application file for complete search history.

(56) References Cited

U.S. PATENT DOCUMENTS

PP19,576 P2 12/2008 Bradford
PP23,718 P3 7/2013 Bradford

*Primary Examiner* — Annette H Para

(57) ABSTRACT

The present invention relates to a plum tree, *Prunus salicina*, and more particularly to a new and distinct variety broadly characterized by a medium size, vigorous, hardy, and productive tree. Being self-unfruitful, the present variety requires cross pollination from an apricot, interspecific, or plum that blooms during the mid season, such as 'Blackred V' interspecific tree (U.S. Plant Pat. No. 19,576). The present variety produces a medium density of flowers that produce a heavy amount of pollen to entice good bee activity to facilitate pollination. The fruit matures under the ecological conditions described during early July, with first picking on Jul. 1, 2021. The fruit is uniformly medium in size, almost black in skin color, very dark red in flesh color, semi-freestone in type, globose to ovate in shape, extremely firm in texture, juicy, very sweet, and excellent in flavor. Also, the fruit is very heat tolerant and can hang firm on the tree for over 3 weeks.

1 Drawing Sheet

Botanical classification: *Prunus salicina.*
Varietal denomination: 'BLACKRED XVI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'BLACKRED XVI'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2014 one such house containing 'Blackred VI' interspecific tree (U.S. Plant Pat. No. 23,718) was crossed by us in this manner. To pollinate this interspecific tree, we selected bouquets from several sources of plum trees without keeping specific written details. Upon reaching maturity the fruit from this interspecific tree was harvested, and the seeds were removed, cracked, stratified and germinated as a group with the label "H28". They were grown as seedlings on their own root in our greenhouse, and upon reaching dormancy transplanted to a cultivated area of our experimental orchard located near Le Grand, Calif. in Merced County (San Joaquin Valley). During the summer of 2018 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Blackred VI' interspecific tree (U.S. Plant Pat. No. 23,718), by being self-unfruitful and by producing fruit that is medium in size but is quite distinguished therefrom by producing fruit that is darker in both skin color and flesh color, that is sweeter in flavor, the is semi-freestone instead of clingstone in type, that can hang firm on the tree longer, and that matures about 10 days later.

The present variety is most similar to 'Blackred V' interspecific tree (U.S. Plant Pat. No. 19,576), by being self-unfruitful and by producing fruit that ripens in early July and that is fairly globose in shape, nearly black in skin color, medium in size, juicy, and excellent in flavor, but is distinguished therefrom by producing fruit that can hang firm longer on the tree, that is more heat tolerant, and that is darker red in flesh color, somewhat sweeter with less acidity in taste, and semi-freestone instead of clingstone in type.

SUMMARY OF VARIETY

The present plum variety is characterized by a medium size, vigorous, hardy, and productive tree. Being self-unfruitful, the present variety requires cross pollination from an apricot, interspecific, or plum that blooms during the mid season, such as 'Blackred V' interspecific tree (U.S. Plant Pat. No. 19,576). The present variety produces a medium density of flowers that produce a heavy amount of pollen to entice good bee activity to facilitate pollination. The fruit matures under the ecological conditions described during early July, with first picking on Jul. 1, 2021. The fruit is uniformly medium in size, almost black in skin color, very dark red in flesh color, semi-freestone in type, globose to ovate in shape, extremely firm in texture, juicy, very sweet, and excellent in flavor. Also, the fruit is very heat tolerant and can hang firm on the tree for over 3 weeks.

DRAWING

The accompanying photograph consists of four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Jul. 13, 2021, on the original tree during its seventh growing season. The flower and bud descriptions were developed during the previous blooming season. All major color code designations are by reference to the Inter-Society Color Council, National Bureau of Standards. Common color names are also used occasionally.

PARENTAGE

Seed parent: Blackred VI (U.S. Plant Pat. No. 23,718) interspecific tree.

Pollen parent: Unknown plum.

TREE

Size: Medium, reaching and maintaining a height of 10' [3.05 m.] and a spread of 6' [1.83 m.] after seven growing seasons utilizing typical dormant pruning.

Vigor: Vigorous, responding typically to irrigation and fertilization. The variety grows about 2' [0.61 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming interspecific or plum, such as 'Blackred V' interspecific tree (U.S. Plant Pat. No. 19,576).

Bearing: Regular bearer, weather dependent, no crop failures observed as of yet.

Trunk:

*Size.*—Medium, reaching a maximum diameter of 4½" [114 mm.] after the seventh growing season.

*Texture.*—Medium to rough.

*Bark color.*—A Moderate yellowish brown [77. m.yBr] and Grayish yellowish brown [80. gy.yBr] variegation with Deep yellowish brown [75. deep yBr] crevices present.

*Lenticels.*—Approximate Number Per Square Inch: 15. Color: Deep orange yellow [69. deep OY]. Average Size: ¼" [6.4 mm.] in length. The width is typically one fourth as much as the length. Shape: Elongated.

Branches:

*Size.*—Medium to slender, scaffold diameter is 2½" [63.5 mm.] measured 12" above the first hanger, limb diameter is 1" [25.4 mm.] measured 12" above the first fork.

*Texture.*—Smooth to medium on first and second year wood, increasing roughness with age.

*Color.*—1st Year Wood Topside: Grayish red [19. gy.R]. 1st Year Wood Underside: Brilliant yellow green [116. brill.YG]. Older Wood: A Grayish brown [61. gy.Br] and Dark brown [59. d.Br] variegation.

*Lenticels.*—Number Per Square Inch: About 25 on second year wood. Color: Moderate orange yellow [71. m.OY]. Average Size: Small, 1/16" [1.6 mm.] in length. The width is typically one fourth as much as the length. Shape: Elongated.

Leaves:

*Size.*—Medium. Average Length: 3⅝" [92.1 mm.]. Average Width: 1 11/16" [42.9 mm.].

*Arrangement.*—Alternate.

*Thickness.*—Medium.

*Form.*—Elliptical.

*Apex.*—Acuminate.

*Base.*—Acute with an average base angle of 70 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Color: Pale greenish yellow [104. p.gY] with some Grayish red [19. gy.R] areas where exposed toward the sun.

*Stipules.*—Number: Mostly 2 per leaf, up to 6 per growing tip. Average Length: ¼" [6.4 mm.]. Color: Moderate greenish yellow [102. m.gY] becoming Grayish red [19. gy.R] with age.

*Glands.*—Number: Mostly 2 per leaf. Position: Alternate, positioned at the intersection of the petiole and base of leaf blade. Form: Globose. Size: Medium, 1/32" [0.8 mm.] in diameter. Color: Grayish greenish yellow [105. gy.gY] becoming Dark brown [59. d.Br] in the center with age. Leaf buds: Pointed.

Flower buds:

*Hardiness.*—Hardy with respect to central California blooming season.

*Diameter.*—Typically 3/16" [4.8 mm.] 1 week before bloom.

*Length.*—Typically ⅜" [9.5 mm.] 1 week before bloom.

*Form.*—Not appressed.
*Surface.*—Very slightly pubescent.
*Tip color.*—White [263. White].

Flowers: Perfect, complete, perigynous, usually a single pistil, typically thirty or more stamens, five sepals and petal locations alternately positioned.
*Average flower diameter.*—1⅜" [34.9 mm.].
*Average flower depth.*—5/16" [7.9 mm.] when fully open.
*Average pedicel length.*—⅜" [9.5 mm.].
*Number of petals.*—Five, no double blossoms observed.
*Petal arrangement.*—Non-overlapping at full bloom.
*Petal shape.*—Oval.
*Petal margin.*—Entire, somewhat wavy.
*Average petal diameter.*—7/16" [11.1 mm.].
*Average petal length.*—9/16" [14.3 mm.].
*Petal apex.*—Rounded.
*Petal base.*—Obtuse.
*Petal color.*—White [263. White] on both sides.
*Anther color.*—Pale orange yellow [73. p.OY].
*Pollen production.*—Heavy, very enticing to bees.
*Pollen color.*—Brilliant yellow [83. brill.Y].
*Stigma color.*—Light greenish yellow [101. l.gY].
*Stigma position.*—Located nearly even with the surrounding anthers.
*Stamen position.*—Typically located about 1/32" [0.8 mm.] below the petals.
*Average pistil length.*—⅝" [15.9 mm.].
*Average stamen length.*—½" [12.7 mm.].
*Ovary.*—Non-pubescent.
*Sepal color.*—Light yellow green [119. l.YG] on both sides.
*Sepal outer surface.*—Very slightly pubescent.
*Sepal length.*—3/16" [4.8 mm.].
*Sepal width.*—⅛" [3.2 mm.].
*Sepal apex.*—Rounded to elliptical to match the width and length.
*Sepal margin.*—Fairly smooth.
*Fragrance.*—Moderate.
*Bloom density.*—Moderate to heavy.
*Number per cluster.*—2 to 6.
*Blooming period.*—Early to medium, blooms with 'Blackred V' (U.S. Plant Pat. No. 19,576) interspecific fruit tree.
*Onset of bloom.*—One percent on Feb. 15, 2021.
*Date of full bloom.*—Feb. 23, 2021.
*Duration of bloom.*—One to two weeks, dependent on ambient temperature.

FRUIT

Maturity when described: Firm ripe, Jul. 13, 2021.
Date of first picking: Jul. 1, 2021.
Date of last picking: Jul. 21, 2021.
Size: Uniform, medium.
*Average diameter axially.*—2½" [63.5 mm.].
*Average diameter across cheek plane.*—2 7/16" [61.9 mm.].
*Average diameter across suture plane.*—2 7/16" [61.9 mm.].
*Typical weight.*—4.6 ounces [131 grams].

Form: Uniform, globose to slightly ovate, fairly symmetrical.
*Longitudinal section form.*—Slightly ovate.
*Axial view form.*—Round.

Suture: A distinct Dark reddish grey [23. d.rGy] line located in a shallow groove extending from the base to just beyond the pistil point.
Ventral surface: Rounded, lipped on both sides.
Lips: Slightly unequal.
Cavity: Flaring.
*Depth.*—7/16" [11.1 mm.].
*Breadth.*—⅞" [22.2 mm.].
Base: Truncate, somewhat cordate if viewed parallel to the suture.
Apex: Rounded.
Pistil point: A Moderate orange yellow [71. m.OY] dot located at the end of the suture of negligible length.
Stem: Medium.
*Average length.*—⅜" [9.5 mm.].
*Average width.*—1/16" [1.6 mm.].
Skin:
*Thickness.*—Medium.
*Surface.*—Smooth.
*Tenacity.*—Tenacious to the flesh.
*Astringency.*—Very slight.
*Tendency to crack.*—None observed.
*Color.*—Reddish black [24. rBlack] with a moderate amount of small Pale yellowish pink [31. p.yPk] freckling throughout.
Flesh:
*Color.*—Very dark red [17. v.d.R] close to the skin smoothly blending to Dark red [16. d.R] toward the stone with Deep red [13. deep R] fibers throughout.
*Surface of pit cavity.*—Covered with Very dark red [17. v.d.R] fibers.
*Amygdalin.*—Moderate.
*Juice.*—Abundant, rich.
*Texture.*—Extremely firm and crisp for over 3 weeks on the tree.
*Heat tolerance.*—Excellent, stays extremely firm during very hot temperatures.
*Fibers.*—Fine, tender.
*Ripens.*—Fairly even.
*Flavor.*—An extremely tasty blend of acid and sugar, typically 24 brix.
*Aroma.*—Very slight.
*Eating quality.*—Excellent.

STONE

Type: Semi-freestone.
Form: Oval.
Hilum: Narrow.
Base: Oblate.
Apex: Rounded.
Tip: Negligible.
Sides: Mostly equal.
Surface: Fairly smooth with rounded ridges toward the base.
External color of stone: Light yellowish brown [76. l.yBr].
Pit wall color when cracked: Light yellowish brown [76. l.yBr].
Cavity surface color: Strong yellowish brown [74. s.yBr].
Average pit wall thickness: 1/16" [1.6 mm.].
Average length: ⅞" [22.2 mm.].
Average width: ¾" [19.1 mm.].

Average breadth: ⅜" [9.5 mm.].

Tendency to split: None observed.

Kernel:

*Form.*—Oval.

*Skin color.*—Dark orange yellow [72. d.OY].

*Pellicle color.*—Pale orange yellow [73. p.OY].

*Vein color.*—Deep yellowish brown [75. deep yBr].

*Taste.*—Bitter.

*Viable.*—Yes.

*Average length.*—9/16" [14.3 mm.].

*Average width.*—7/16" [11.1 mm.].

*Amygdalin.*—Moderate.

USE

Market: Fresh market and long distance shipping.

Keeping quality: Good, fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Blackred V' interspecific tree (U.S. Plant Pat. No. 19,576), by being self-unfruitful and by producing fruit that ripens in early July and that is fairly globose in shape, nearly black in skin color, medium in size, juicy, and excellent in flavor, but is distinguished therefrom by producing fruit that can hang firm longer on the tree, that is more heat tolerant, and that is darker red in flesh color, somewhat sweeter with less acidity in taste, and semi-freestone instead of clingstone in type.

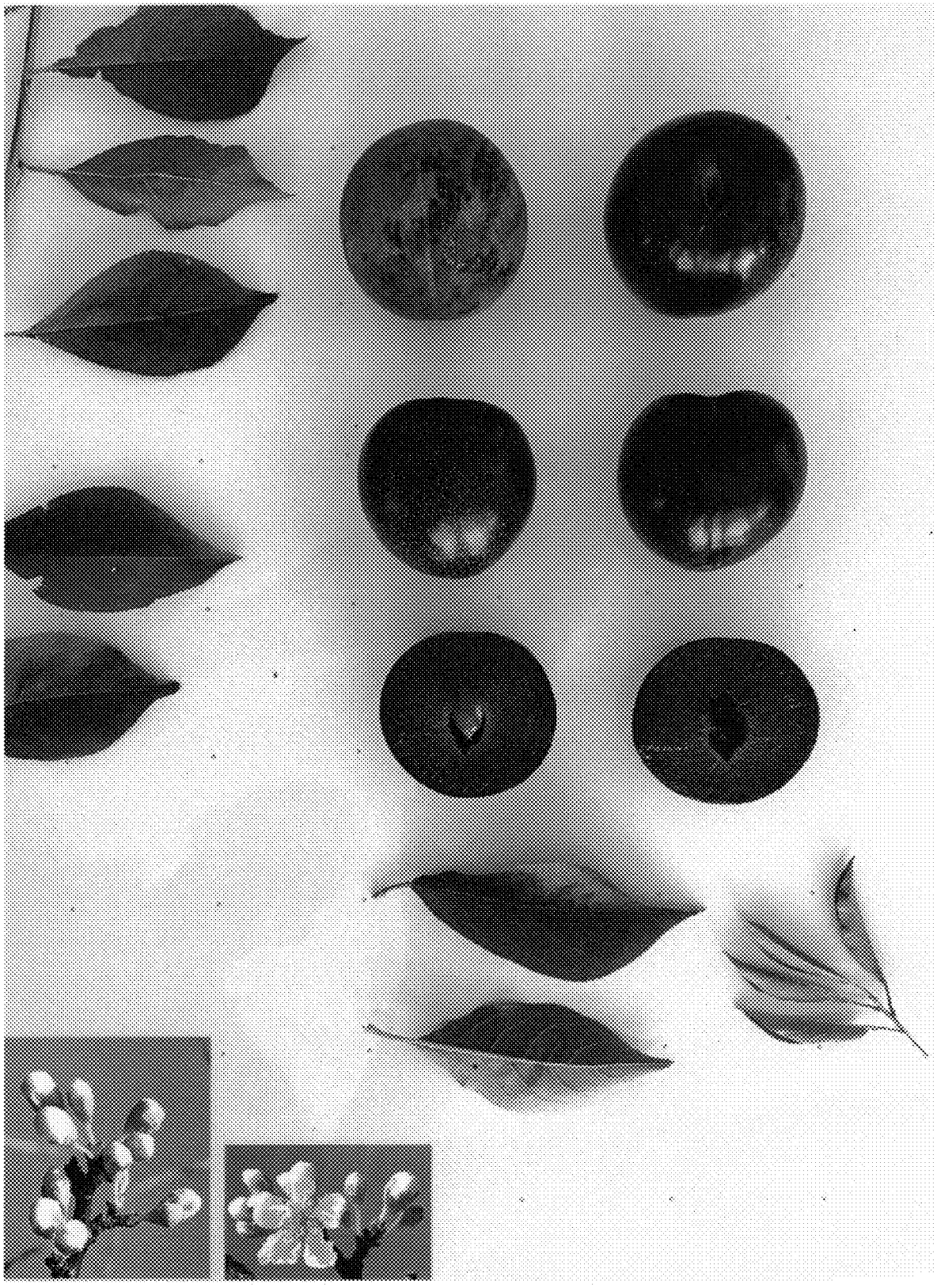

* * * * *